(12) United States Patent
Hans et al.

(10) Patent No.: US 10,736,829 B2
(45) Date of Patent: Aug. 11, 2020

(54) USE OF CERTAIN HYDROXYBENZOIC ACID AMIDES FOR MASKING UNPLEASANT TASTE IMPRESSIONS

(71) Applicant: SYMRISE AG, Holzminden (DE)

(72) Inventors: Joachim Hans, Holzminden (DE); Jakob Ley, Holzminden (DE); Kathrin Langer, Dassel (DE); Susanne Paetz, Höxter (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 15/764,525

(22) PCT Filed: Sep. 30, 2015

(86) PCT No.: PCT/EP2015/072620
§ 371 (c)(1),
(2) Date: Mar. 29, 2018

(87) PCT Pub. No.: WO2017/054866
PCT Pub. Date: Apr. 6, 2017

(65) Prior Publication Data
US 2018/0311132 A1    Nov. 1, 2018

(51) Int. Cl.
| | |
|---|---|
| *A61K 8/42* | (2006.01) |
| *A23L 27/00* | (2016.01) |
| *A23L 27/20* | (2016.01) |
| *A61K 8/44* | (2006.01) |
| *A61K 8/64* | (2006.01) |
| *A23L 33/18* | (2016.01) |
| *A23L 33/175* | (2016.01) |
| *A61Q 11/00* | (2006.01) |

(52) U.S. Cl.
CPC .............. *A61K 8/42* (2013.01); *A23L 27/204* (2016.08); *A23L 27/86* (2016.08); *A23L 33/175* (2016.08); *A23L 33/18* (2016.08); *A61K 8/445* (2013.01); *A61K 8/64* (2013.01); *A61Q 11/00* (2013.01); *A23V 2002/00* (2013.01); *A23V 2200/16* (2013.01); *A23V 2250/065* (2013.01); *A23V 2250/0626* (2013.01); *A23V 2250/0628* (2013.01); *A23V 2250/0638* (2013.01); *A23V 2250/0654* (2013.01)

(58) Field of Classification Search
None
See application file for complete search history.

(56) References Cited

U.S. PATENT DOCUMENTS

| | | | |
|---|---|---|---|
| 2003/0044466 A1* | 3/2003 | Markey | A61K 9/0065 424/469 |
| 2008/0214675 A1* | 9/2008 | Ley | A61K 8/42 514/622 |
| 2011/0158919 A1 | 6/2011 | Kennison et al. | |

FOREIGN PATENT DOCUMENTS

| | | |
|---|---|---|
| DE | 102004041496 A1 | 3/2006 |
| EP | 2386211 A1 | 11/2011 |
| WO | 2006024587 A1 | 3/2006 |

OTHER PUBLICATIONS

Fujukami et al. Agricultural and Biological Chemistry 1968 32(6):794-795 (Year: 1968).*
Matar et al. "Biologically Active Peptides Released in Fermented Milk: Role and Functions" in Handbook of Fermented Functional Foods. Farnworth ed. CRC Press: Boca Raton 2003 p. 177-201 (Year: 2003).*
International Search Report and Written Opinion dated Sep. 6, 2016 for corresponding application No. PCT/EP2015/072620.

* cited by examiner

*Primary Examiner* — Robert A Wax
*Assistant Examiner* — Caralynne E Helm
(74) *Attorney, Agent, or Firm* — Polsinelli PC

(57) ABSTRACT

The present invention relates primarily to the use of certain hydroxybenzoic acid amides or the salts or mixtures thereof for masking an unpleasant taste impression, preferably of a bitter, adstringent, dusty, dry, floury, rancid, metallic and/or cardboard taste or aftertaste, of one or more unpleasant-tasting peptides or of certain amino acid mixtures. The invention further relates to a corresponding method for masking unpleasant taste impressions and to novel preparations.

2 Claims, No Drawings

Specification includes a Sequence Listing.

SEQUENCE LISTING

```
<160> NUMBER OF SEQ ID NOS: 84

<210> SEQ ID NO 1
<211> LENGTH: 12
<212> TYPE: PRT
<213> ORGANISM: artificial sequence
<220> FEATURE:
<223> OTHER INFORMATION: peptide sequence

<400> SEQUENCE: 1

Gly Lys His Gln Gln Glu Glu Glu Asn Glu Gly Gly
1               5                   10

<210> SEQ ID NO 2
<211> LENGTH: 11
<212> TYPE: PRT
<213> ORGANISM: artificial sequence
<220> FEATURE:
<223> OTHER INFORMATION: peptide sequence

<400> SEQUENCE: 2

Asn Phe Asn Asn Gln Leu Asp Gln Thr Pro Arg
1               5                   10

<210> SEQ ID NO 3
<211> LENGTH: 10
<212> TYPE: PRT
<213> ORGANISM: artificial sequence
<220> FEATURE:
<223> OTHER INFORMATION: peptide sequence

<400> SEQUENCE: 3

Ala Gly Asn Pro Asp Ile Glu His Pro Glu
1               5                   10

<210> SEQ ID NO 4
<211> LENGTH: 10
<212> TYPE: PRT
<213> ORGANISM: artificial sequence
<220> FEATURE:
<223> OTHER INFORMATION: peptide sequence

<400> SEQUENCE: 4

Asn Ala Leu Glu Pro Asp His Arg Val Glu
1               5                   10
```

```
<210> SEQ ID NO 5
<211> LENGTH: 8
<212> TYPE: PRT
<213> ORGANISM: artificial sequence
<220> FEATURE:
<223> OTHER INFORMATION: peptide sequence

<400> SEQUENCE: 5

Gly Asn Pro Asp Ile Glu His Pro
1               5

<210> SEQ ID NO 6
<211> LENGTH: 8
<212> TYPE: PRT
<213> ORGANISM: artificial sequence
<220> FEATURE:
<223> OTHER INFORMATION: peptide sequence

<400> SEQUENCE: 6

Ile Tyr Pro Gly Cys Pro Ser Thr
1               5

<210> SEQ ID NO 7
<211> LENGTH: 8
<212> TYPE: PRT
<213> ORGANISM: artificial sequence
<220> FEATURE:
<223> OTHER INFORMATION: peptide sequence

<400> SEQUENCE: 7

Lys Leu His Glu Asn Ile Ala Arg
1               5

<210> SEQ ID NO 8
<211> LENGTH: 8
<212> TYPE: PRT
<213> ORGANISM: artificial sequence
<220> FEATURE:
<223> OTHER INFORMATION: peptide sequence

<400> SEQUENCE: 8

Leu Ala Gly Asn Gln Glu Gln Glu
1               5

<210> SEQ ID NO 9
<211> LENGTH: 7
<212> TYPE: PRT
<213> ORGANISM: artificial sequence
<220> FEATURE:
<223> OTHER INFORMATION: peptide sequence

<400> SEQUENCE: 9

Ala Leu Glu Pro Asp His Arg
1               5

<210> SEQ ID NO 10
<211> LENGTH: 7
<212> TYPE: PRT
<213> ORGANISM: artificial sequence
<220> FEATURE:
<223> OTHER INFORMATION: peptide sequence

<400> SEQUENCE: 10

Glu Gln Gly Gly Glu Gln Gly
1               5

<210> SEQ ID NO 11
```

```
<211> LENGTH: 7
<212> TYPE: PRT
<213> ORGANISM: artificial sequence
<220> FEATURE:
<223> OTHER INFORMATION: peptide sequence

<400> SEQUENCE: 11

Glu Gln Pro Gln Gln Asn Glu
1               5

<210> SEQ ID NO 12
<211> LENGTH: 7
<212> TYPE: PRT
<213> ORGANISM: artificial sequence
<220> FEATURE:
<223> OTHER INFORMATION: peptide sequence

<400> SEQUENCE: 12

Ile Gly Thr Leu Ala Gly Ala
1               5

<210> SEQ ID NO 13
<211> LENGTH: 7
<212> TYPE: PRT
<213> ORGANISM: artificial sequence
<220> FEATURE:
<223> OTHER INFORMATION: peptide sequence

<400> SEQUENCE: 13

Asn Ala Met Phe Val Pro His
1               5

<210> SEQ ID NO 14
<211> LENGTH: 6
<212> TYPE: PRT
<213> ORGANISM: artificial sequence
<220> FEATURE:
<223> OTHER INFORMATION: peptide sequence

<400> SEQUENCE: 14

Gly Met Ile Tyr Pro Gly
1               5

<210> SEQ ID NO 15
<211> LENGTH: 6
<212> TYPE: PRT
<213> ORGANISM: artificial sequence
<220> FEATURE:
<223> OTHER INFORMATION: peptide sequence

<400> SEQUENCE: 15

His Asn Ile Gly Gln Thr
1               5

<210> SEQ ID NO 16
<211> LENGTH: 6
<212> TYPE: PRT
<213> ORGANISM: artificial sequence
<220> FEATURE:
<223> OTHER INFORMATION: peptide sequence

<400> SEQUENCE: 16

Ile Tyr Pro Gly Cys Pro
1               5

<210> SEQ ID NO 17
<211> LENGTH: 6
```

```
<212> TYPE: PRT
<213> ORGANISM: artificial sequence
<220> FEATURE:
<223> OTHER INFORMATION: peptide sequence

<400> SEQUENCE: 17

Asn Ala Leu Lys Pro Asp
1               5

<210> SEQ ID NO 18
<211> LENGTH: 5
<212> TYPE: PRT
<213> ORGANISM: artificial sequence
<220> FEATURE:
<223> OTHER INFORMATION: peptide sequence

<400> SEQUENCE: 18

Phe Ile Gln Gly Val
1               5

<210> SEQ ID NO 19
<211> LENGTH: 5
<212> TYPE: PRT
<213> ORGANISM: artificial sequence
<220> FEATURE:
<223> OTHER INFORMATION: peptide sequence

<400> SEQUENCE: 19

Asn Ala Leu Pro Glu
1               5

<210> SEQ ID NO 20
<211> LENGTH: 5
<212> TYPE: PRT
<213> ORGANISM: artificial sequence
<220> FEATURE:
<223> OTHER INFORMATION: peptide sequence

<400> SEQUENCE: 20

Asn Asn Glu Asp Thr
1               5

<210> SEQ ID NO 21
<211> LENGTH: 5
<212> TYPE: PRT
<213> ORGANISM: artificial sequence
<220> FEATURE:
<223> OTHER INFORMATION: peptide sequence

<400> SEQUENCE: 21

Ser Ala Glu Phe Gly
1               5

<210> SEQ ID NO 22
<211> LENGTH: 5
<212> TYPE: PRT
<213> ORGANISM: artificial sequence
<220> FEATURE:
<223> OTHER INFORMATION: peptide sequence

<400> SEQUENCE: 22

Ser Ile Ile Asp Thr
1               5

<210> SEQ ID NO 23
<211> LENGTH: 5
<212> TYPE: PRT
```

```
<213> ORGANISM: artificial sequence
<220> FEATURE:
<223> OTHER INFORMATION: peptide sequence

<400> SEQUENCE: 23

Tyr Glu Gly Asn Ser
1               5

<210> SEQ ID NO 24
<211> LENGTH: 4
<212> TYPE: PRT
<213> ORGANISM: artificial sequence
<220> FEATURE:
<223> OTHER INFORMATION: peptide sequence

<400> SEQUENCE: 24

Leu Leu Leu Leu
1

<210> SEQ ID NO 25
<211> LENGTH: 4
<212> TYPE: PRT
<213> ORGANISM: artificial sequence
<220> FEATURE:
<223> OTHER INFORMATION: peptide sequence

<400> SEQUENCE: 25

Asn Leu Gln Gly
1

<210> SEQ ID NO 26
<211> LENGTH: 4
<212> TYPE: PRT
<213> ORGANISM: artificial sequence
<220> FEATURE:
<223> OTHER INFORMATION: peptide sequence

<400> SEQUENCE: 26

Ser Asp Asn Phe
1

<210> SEQ ID NO 27
<211> LENGTH: 15
<212> TYPE: PRT
<213> ORGANISM: artificial sequence
<220> FEATURE:
<223> OTHER INFORMATION: peptide sequence

<400> SEQUENCE: 27

Val Glu Glu Leu Lys Pro Thr Pro Glu Gly Asp Leu Glu Ile Leu
1               5                   10                  15

<210> SEQ ID NO 28
<211> LENGTH: 13
<212> TYPE: PRT
<213> ORGANISM: artificial sequence
<220> FEATURE:
<223> OTHER INFORMATION: peptide sequence

<400> SEQUENCE: 28

Gln Leu Phe Gly Pro Asn Val Asn Pro Trp His Asn Pro
1               5                   10

<210> SEQ ID NO 29
<211> LENGTH: 13
<212> TYPE: PRT
<213> ORGANISM: artificial sequence
```

```
<220> FEATURE:
<223> OTHER INFORMATION: peptide sequence

<400> SEQUENCE: 29

Gln Leu Phe Asn Pro Ser Thr Asn Pro Trp His Ser Pro
1               5                   10

<210> SEQ ID NO 30
<211> LENGTH: 11
<212> TYPE: PRT
<213> ORGANISM: artificial sequence
<220> FEATURE:
<223> OTHER INFORMATION: peptide sequence

<400> SEQUENCE: 30

Gly Gly Arg Gly Pro Pro Phe Ile Val Gly Gly
1               5                   10

<210> SEQ ID NO 31
<211> LENGTH: 11
<212> TYPE: PRT
<213> ORGANISM: artificial sequence
<220> FEATURE:
<223> OTHER INFORMATION: peptide sequence

<400> SEQUENCE: 31

Gln Leu Phe Asn Pro Ser Thr Asn Pro Trp His
1               5                   10

<210> SEQ ID NO 32
<211> LENGTH: 9
<212> TYPE: PRT
<213> ORGANISM: artificial sequence
<220> FEATURE:
<223> OTHER INFORMATION: peptide sequence

<400> SEQUENCE: 32

Gly Gly Arg Gly Pro Pro Phe Ile Val
1               5

<210> SEQ ID NO 33
<211> LENGTH: 9
<212> TYPE: PRT
<213> ORGANISM: artificial sequence
<220> FEATURE:
<223> OTHER INFORMATION: peptide sequence

<400> SEQUENCE: 33

Gln Leu Phe Asn Pro Ser Thr Asn Pro
1               5

<210> SEQ ID NO 34
<211> LENGTH: 9
<212> TYPE: PRT
<213> ORGANISM: artificial sequence
<220> FEATURE:
<223> OTHER INFORMATION: peptide sequence

<400> SEQUENCE: 34

Arg Gly Pro Pro Phe Ile Val Gly Gly
1               5

<210> SEQ ID NO 35
<211> LENGTH: 9
<212> TYPE: PRT
<213> ORGANISM: artificial sequence
<220> FEATURE:
```

<223> OTHER INFORMATION: peptide sequence

<400> SEQUENCE: 35

Arg Gly Pro Pro Gly Gly Gly Phe Phe
1               5

<210> SEQ ID NO 36
<211> LENGTH: 8
<212> TYPE: PRT
<213> ORGANISM: artificial sequence
<220> FEATURE:
<223> OTHER INFORMATION: peptide sequence

<400> SEQUENCE: 36

Gly Gly Arg Pro Phe Phe Gly Gly
1               5

<210> SEQ ID NO 37
<211> LENGTH: 6
<212> TYPE: PRT
<213> ORGANISM: artificial sequence
<220> FEATURE:
<223> OTHER INFORMATION: peptide sequence

<400> SEQUENCE: 37

Gln Leu Phe Asn Pro Ser
1               5

<210> SEQ ID NO 38
<211> LENGTH: 27
<212> TYPE: PRT
<213> ORGANISM: artificial sequence
<220> FEATURE:
<223> OTHER INFORMATION: peptide sequence

<400> SEQUENCE: 38

Ala Gln Thr Gln Ser Leu Val Tyr Pro Phe Pro Gly Pro Ile Pro Asn
1               5                   10                  15

Ser Leu Pro Gln Asn Ile Pro Pro Leu Thr Gln
            20                  25

<210> SEQ ID NO 39
<211> LENGTH: 17
<212> TYPE: PRT
<213> ORGANISM: artificial sequence
<220> FEATURE:
<223> OTHER INFORMATION: peptide sequence

<400> SEQUENCE: 39

Tyr Gln Gln Pro Val Leu Gly Pro Val Arg Gly Pro Phe Pro Ile Ile
1               5                   10                  15

Val

<210> SEQ ID NO 40
<211> LENGTH: 14
<212> TYPE: PRT
<213> ORGANISM: artificial sequence
<220> FEATURE:
<223> OTHER INFORMATION: peptide sequence

<400> SEQUENCE: 40

Pro Val Leu Gly Pro Val Arg Gly Pro Phe Pro Ile Ile Val
1               5                   10

<210> SEQ ID NO 41

```
<211> LENGTH: 13
<212> TYPE: PRT
<213> ORGANISM: artificial sequence
<220> FEATURE:
<223> OTHER INFORMATION: peptide sequence

<400> SEQUENCE: 41

Ser Leu Val Tyr Pro Phe Pro Gly Pro Ile His Asn Ser
 1               5                  10

<210> SEQ ID NO 42
<211> LENGTH: 13
<212> TYPE: PRT
<213> ORGANISM: artificial sequence
<220> FEATURE:
<223> OTHER INFORMATION: peptide sequence

<400> SEQUENCE: 42

Val Pro Leu Gly Thr Gln Tyr Thr Asp Ala Pro Ser Phe
 1               5                  10

<210> SEQ ID NO 43
<211> LENGTH: 12
<212> TYPE: PRT
<213> ORGANISM: artificial sequence
<220> FEATURE:
<223> OTHER INFORMATION: peptide sequence

<400> SEQUENCE: 43

Phe Phe Val Ala Pro Phe Pro Glu Val Phe Gly Lys
 1               5                  10

<210> SEQ ID NO 44
<211> LENGTH: 12
<212> TYPE: PRT
<213> ORGANISM: artificial sequence
<220> FEATURE:
<223> OTHER INFORMATION: peptide sequence

<400> SEQUENCE: 44

Phe Phe Val Ala Pro Phe Pro Gln Val Phe Gly Lys
 1               5                  10

<210> SEQ ID NO 45
<211> LENGTH: 11
<212> TYPE: PRT
<213> ORGANISM: artificial sequence
<220> FEATURE:
<223> OTHER INFORMATION: peptide sequence

<400> SEQUENCE: 45

Leu Val Tyr Pro Phe Pro Gly Pro Ile His Asn
 1               5                  10

<210> SEQ ID NO 46
<211> LENGTH: 10
<212> TYPE: PRT
<213> ORGANISM: artificial sequence
<220> FEATURE:
<223> OTHER INFORMATION: peptide sequence

<400> SEQUENCE: 46

Pro Val Arg Gly Pro Phe Pro Ile Ile Val
 1               5                  10

<210> SEQ ID NO 47
<211> LENGTH: 10
```

```
<212> TYPE: PRT
<213> ORGANISM: artificial sequence
<220> FEATURE:
<223> OTHER INFORMATION: peptide sequence

<400> SEQUENCE: 47

Val Tyr Pro Phe Pro Gly Pro Ile Pro Asn
1               5                   10

<210> SEQ ID NO 48
<211> LENGTH: 10
<212> TYPE: PRT
<213> ORGANISM: artificial sequence
<220> FEATURE:
<223> OTHER INFORMATION: peptide sequence

<400> SEQUENCE: 48

Val Tyr Pro Phe Pro Pro Ile Gly Asn His
1               5                   10

<210> SEQ ID NO 49
<211> LENGTH: 10
<212> TYPE: PRT
<213> ORGANISM: artificial sequence
<220> FEATURE:
<223> OTHER INFORMATION: peptide sequence

<400> SEQUENCE: 49

Tyr Leu Gly Tyr Leu Glu Gln Leu Leu Arg
1               5                   10

<210> SEQ ID NO 50
<211> LENGTH: 10
<212> TYPE: PRT
<213> ORGANISM: artificial sequence
<220> FEATURE:
<223> OTHER INFORMATION: peptide sequence

<400> SEQUENCE: 50

Tyr Pro Phe Pro Gly Pro Ile His Asn Ser
1               5                   10

<210> SEQ ID NO 51
<211> LENGTH: 10
<212> TYPE: PRT
<213> ORGANISM: artificial sequence
<220> FEATURE:
<223> OTHER INFORMATION: peptide sequence

<400> SEQUENCE: 51

Tyr Pro Phe Pro Gly Pro Ile Pro Asn Ser
1               5                   10

<210> SEQ ID NO 52
<211> LENGTH: 9
<212> TYPE: PRT
<213> ORGANISM: artificial sequence
<220> FEATURE:
<223> OTHER INFORMATION: peptide sequence

<400> SEQUENCE: 52

Pro Phe Pro Gly Pro Ile Pro Asn Ser
1               5

<210> SEQ ID NO 53
<211> LENGTH: 9
<212> TYPE: PRT
```

```
<213> ORGANISM: artificial sequence
<220> FEATURE:
<223> OTHER INFORMATION: peptide sequence

<400> SEQUENCE: 53

Tyr Pro Phe Pro Gly Pro His Ile Asn
1               5

<210> SEQ ID NO 54
<211> LENGTH: 9
<212> TYPE: PRT
<213> ORGANISM: artificial sequence
<220> FEATURE:
<223> OTHER INFORMATION: peptide sequence

<400> SEQUENCE: 54

Tyr Pro Phe Pro Gly Pro Ile Pro Asn
1               5

<210> SEQ ID NO 55
<211> LENGTH: 8
<212> TYPE: PRT
<213> ORGANISM: artificial sequence
<220> FEATURE:
<223> OTHER INFORMATION: peptide sequence

<400> SEQUENCE: 55

Phe Ala Leu Pro Gln Tyr Leu Lys
1               5

<210> SEQ ID NO 56
<211> LENGTH: 8
<212> TYPE: PRT
<213> ORGANISM: artificial sequence
<220> FEATURE:
<223> OTHER INFORMATION: peptide sequence

<400> SEQUENCE: 56

Gly Pro Val Arg Gly Pro Phe Pro
1               5

<210> SEQ ID NO 57
<211> LENGTH: 8
<212> TYPE: PRT
<213> ORGANISM: artificial sequence
<220> FEATURE:
<223> OTHER INFORMATION: peptide sequence

<400> SEQUENCE: 57

Leu Gly Tyr Leu Glu Gln Leu Leu
1               5

<210> SEQ ID NO 58
<211> LENGTH: 8
<212> TYPE: PRT
<213> ORGANISM: artificial sequence
<220> FEATURE:
<223> OTHER INFORMATION: peptide sequence

<400> SEQUENCE: 58

Arg Gly Pro Phe Pro Ile Ile Val
1               5

<210> SEQ ID NO 59
<211> LENGTH: 8
<212> TYPE: PRT
<213> ORGANISM: artificial sequence
```

```
<220> FEATURE:
<223> OTHER INFORMATION: peptide sequence

<400> SEQUENCE: 59

Arg Gly Pro Gly Pro Ile Ile Val
1               5

<210> SEQ ID NO 60
<211> LENGTH: 7
<212> TYPE: PRT
<213> ORGANISM: artificial sequence
<220> FEATURE:
<223> OTHER INFORMATION: peptide sequence

<400> SEQUENCE: 60

Ala Pro Phe Pro Glu Val Phe
1               5

<210> SEQ ID NO 61
<211> LENGTH: 7
<212> TYPE: PRT
<213> ORGANISM: artificial sequence
<220> FEATURE:
<223> OTHER INFORMATION: peptide sequence

<400> SEQUENCE: 61

Ala Tyr Phe Tyr Pro Glu Leu
1               5

<210> SEQ ID NO 62
<211> LENGTH: 7
<212> TYPE: PRT
<213> ORGANISM: artificial sequence
<220> FEATURE:
<223> OTHER INFORMATION: peptide sequence

<400> SEQUENCE: 62

Phe Tyr Pro Glu Leu Phe Arg
1               5

<210> SEQ ID NO 63
<211> LENGTH: 7
<212> TYPE: PRT
<213> ORGANISM: artificial sequence
<220> FEATURE:
<223> OTHER INFORMATION: peptide sequence

<400> SEQUENCE: 63

Pro Phe Pro Gly Pro Ile Pro
1               5

<210> SEQ ID NO 64
<211> LENGTH: 7
<212> TYPE: PRT
<213> ORGANISM: artificial sequence
<220> FEATURE:
<223> OTHER INFORMATION: peptide sequence

<400> SEQUENCE: 64

Arg Gly Pro Phe Pro Ile Val
1               5

<210> SEQ ID NO 65
<211> LENGTH: 7
<212> TYPE: PRT
<213> ORGANISM: artificial sequence
<220> FEATURE:
```

<223> OTHER INFORMATION: peptide sequence

<400> SEQUENCE: 65

Tyr Pro Phe Pro Gly Pro Ile
1               5

<210> SEQ ID NO 66
<211> LENGTH: 6
<212> TYPE: PRT
<213> ORGANISM: artificial sequence
<220> FEATURE:
<223> OTHER INFORMATION: peptide sequence

<400> SEQUENCE: 66

Pro Val Leu Gly Pro Val
1               5

<210> SEQ ID NO 67
<211> LENGTH: 6
<212> TYPE: PRT
<213> ORGANISM: artificial sequence
<220> FEATURE:
<223> OTHER INFORMATION: peptide sequence

<400> SEQUENCE: 67

Val Arg Gly Pro Phe Pro
1               5

<210> SEQ ID NO 68
<211> LENGTH: 6
<212> TYPE: PRT
<213> ORGANISM: artificial sequence
<220> FEATURE:
<223> OTHER INFORMATION: peptide sequence

<400> SEQUENCE: 68

Phe Tyr Pro Glu Leu Phe
1               5

<210> SEQ ID NO 69
<211> LENGTH: 6
<212> TYPE: PRT
<213> ORGANISM: artificial sequence
<220> FEATURE:
<223> OTHER INFORMATION: peptide sequence

<400> SEQUENCE: 69

Gly Pro Phe Pro Ile Val
1               5

<210> SEQ ID NO 70
<211> LENGTH: 6
<212> TYPE: PRT
<213> ORGANISM: artificial sequence
<220> FEATURE:
<223> OTHER INFORMATION: peptide sequence

<400> SEQUENCE: 70

Pro Phe Pro Gly Pro Ile
1               5

<210> SEQ ID NO 71
<211> LENGTH: 6
<212> TYPE: PRT
<213> ORGANISM: artificial sequence
<220> FEATURE:
<223> OTHER INFORMATION: peptide sequence

<400> SEQUENCE: 71

Pro Phe Pro Ile Ile Val
1               5

<210> SEQ ID NO 72
<211> LENGTH: 5
<212> TYPE: PRT
<213> ORGANISM: artificial sequence
<220> FEATURE:
<223> OTHER INFORMATION: peptide sequence

<400> SEQUENCE: 72

Asp Ile Lys Gln Met
1               5

<210> SEQ ID NO 73
<211> LENGTH: 5
<212> TYPE: PRT
<213> ORGANISM: artificial sequence
<220> FEATURE:
<223> OTHER INFORMATION: peptide sequence

<400> SEQUENCE: 73

Glu Ile Val Pro Asn
1               5

<210> SEQ ID NO 74
<211> LENGTH: 5
<212> TYPE: PRT
<213> ORGANISM: artificial sequence
<220> FEATURE:
<223> OTHER INFORMATION: peptide sequence

<400> SEQUENCE: 74

Asn Glu Asn Leu Leu
1               5

<210> SEQ ID NO 75
<211> LENGTH: 5
<212> TYPE: PRT
<213> ORGANISM: artificial sequence
<220> FEATURE:
<223> OTHER INFORMATION: peptide sequence

<400> SEQUENCE: 75

Pro Gly Pro Ile Pro
1               5

<210> SEQ ID NO 76
<211> LENGTH: 4
<212> TYPE: PRT
<213> ORGANISM: artificial sequence
<220> FEATURE:
<223> OTHER INFORMATION: peptide sequence

<400> SEQUENCE: 76

Glu Val Leu Asn
1

<210> SEQ ID NO 77
<211> LENGTH: 4
<212> TYPE: PRT
<213> ORGANISM: artificial sequence
<220> FEATURE:
<223> OTHER INFORMATION: peptide sequence

```
<400> SEQUENCE: 77

Leu Pro Gln Glu
 1

<210> SEQ ID NO 78
<211> LENGTH: 4
<212> TYPE: PRT
<213> ORGANISM: artificial sequence
<220> FEATURE:
<223> OTHER INFORMATION: peptide sequence

<400> SEQUENCE: 78

Val Tyr Pro Phe
 1

<210> SEQ ID NO 79
<211> LENGTH: 6
<212> TYPE: PRT
<213> ORGANISM: artificial sequence
<220> FEATURE:
<223> OTHER INFORMATION: peptide sequence

<400> SEQUENCE: 79

Gly Pro Phe Pro Val Ile
 1               5

<210> SEQ ID NO 80
<211> LENGTH: 8
<212> TYPE: PRT
<213> ORGANISM: artificial sequence
<220> FEATURE:
<223> OTHER INFORMATION: peptide sequence

<400> SEQUENCE: 80

Phe Ala Leu Pro Glu Tyr Leu Lys
 1               5

<210> SEQ ID NO 81
<211> LENGTH: 7
<212> TYPE: PRT
<213> ORGANISM: artificial sequence
<220> FEATURE:
<223> OTHER INFORMATION: peptide sequence

<400> SEQUENCE: 81

Arg Gly Pro Pro Phe Ile Val
 1               5

<210> SEQ ID NO 82
<211> LENGTH: 4
<212> TYPE: PRT
<213> ORGANISM: artificial sequence
<220> FEATURE:
<223> OTHER INFORMATION: peptide sequence

<400> SEQUENCE: 82

Tyr Pro Phe Pro
 1

<210> SEQ ID NO 83
<211> LENGTH: 5
<212> TYPE: PRT
<213> ORGANISM: artificial sequence
<220> FEATURE:
<223> OTHER INFORMATION: peptide sequence

<400> SEQUENCE: 83
```

```
Ile Pro Ala Val Phe
1               5

<210> SEQ ID NO 84
<211> LENGTH: 4
<212> TYPE: PRT
<213> ORGANISM: artificial sequence
<220> FEATURE:
<223> OTHER INFORMATION: peptide sequence

<400> SEQUENCE: 84

Tyr Gly Leu Phe
1
```

USE OF CERTAIN HYDROXYBENZOIC ACID AMIDES FOR MASKING UNPLEASANT TASTE IMPRESSIONS

CROSS-REFERENCE TO RELATED APPLICATIONS

This application is a national stage application (under 35 U.S.C. § 371) of PCT/EP2015/072620, filed Sep. 30, 2015, which is incorporated herein by reference in its entirety.

SEQUENCE LISTING SUBMISSION VIA EFS-WEB

A computer readable text file, entitled "revised-eolf-othd-000001.txt", created on or about Jul. 11, 2018, with a file size of about 16 KB contains the sequence listing for this application and is hereby incorporated by reference in its entirety.

The present invention primarily relates to the use of certain hydroxybenzoic acid amides, their salts and their mixtures for masking an unpleasant taste impression, preferably a bitter, astringent, cloggy, dusty, dry, floury, rancid and/or metallic taste or aftertaste, of one or more certain unpleasant tasting peptides or certain amino acid mixtures.

Furthermore, the invention relates to corresponding methods for masking unpleasant taste impressions and to new compositions.

Further aspects of the present invention result from the subsequent description, the examples as well as particularly the attached claims.

Foodstuff and luxury foods often contain diverse bitter substances, which are on the one side desired in moderation and which are characteristic (e.g. caffeine in tea or coffee, quinine in so-called bitter lemon drinks or hop extracts in beer), but which can on the other side strongly reduce the value (e.g. flavonoid glycosides and limonoids in citrus juices; bitter aftertaste of many artificial sweeteners such as aspartame or saccharine; hydrophobic amino acids and/or peptides in cheese). (Bitter) Peptides are often found as mixtures in protein hydrolysates, particularly hydrolysates of milk proteins or fractions thereof (such as the casein or whey fraction), which are also usually added to foodstuff (sports nutrition, etc.). Also, peptides, which can arise during cheese maturation, are often described as bitter. Also, hydrolysates of plant protein fractions (soy, alfalfa, pea, bean, lupins, etc.) are often characterized by a bitter taste.

For allowing to maintain the quality determining and necessary ingredients (e.g. amino acids or peptides) in foodstuff, it is desired to find substances, which can effectively suppress or at least reduce the unpleasant taste impressions, particularly bitter, astringent and/or metallic taste impressions.

Several substances, which can (partially) suppress the bitter taste, are known already, however, many of these show strong limitations in their use.

Dong et al. (CN101147800) describe the masking the bitter taste of casein phosphopeptides by complexing with cyclodextrans, however, this method is highly specific for the used phosphopetides.

Tanisawa et al. (JP 2009 278,917) describe the use of an edible coagulation agent for de-bittering of foodstuff, whereby, however, the bioavailability of the bitter substances may possibly be negatively affected.

Urata et al. (JP 2011 162,539) describe the use of a stilbene containing plant extract in connection with branched chained cyclodextrins for masking the bitter taste of milk peptides.

Hamaguchi et al. (JP 2012 110,248) describe the use of polyamino acids with a molecular weight of at least 500 Da for masking the bitter taste of drinks and foodstuff.

However, there is the constant need to find substances, which are suitable for masking unpleasant taste impressions of certain substances, particularly such substances, which are easily accessible. Preferably such substances shall be listed, which reduce or even completely suppress in very low concentrations the unpleasant taste impression, wherein it is particularly advantageous, if the substances in such a concentration do not show almost any original taste and thus do not influence further, usually not unpleasant taste qualities.

The present invention is based on the object to find such substances.

The above object is achieved according to the invention by use of one, two or more different hydroxybenzoic acid amides of formula (I)

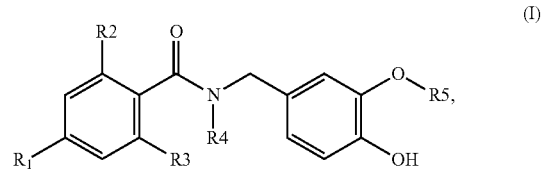

wherein
$R^1$ and $R^2$ denote independent of each other hydrogen, hydroxyl or methoxy, preferably hydrogen or hydroxyl, with the provision that at least one of the groups $R^1$ or $R^2$ denote hydroxyl,
and
either
  $R^3$ denotes hydrogen or hydroxyl, preferably hydrogen, and
  $R^4$ denotes hydrogen
or
  $R^3$ and $R^4$ together denote a group —O—C(=O)— and thus form a ring in form of a cyclic carbamate, and
  $R^5$ denotes hydrogen or methyl, preferably methyl,
or
of one, two or more different salts of one, two or more different hydroxybenzoic acid amides of formula (I) as defined above
or
of a mixture of one, two or more different hydroxybenzoic acid amides of formula (I) as defined above with one, two or more different salts of one, two or more different hydroxybenzoic acid amides of formula (I) as defined above for masking an unpleasant taste impression, preferably a bitter, astringent, doggy, dusty, dry, floury, rancid and/or metallic taste or aftertaste, of one or more unpleasant tasting substances, wherein the or, respectively, one, more or all of the unpleasant tastes is/are selected from the group consisting of amino acid mixtures comprising or consisting of, each related to the weight, 40 to 50 parts L-leucine, 20 to 30 parts L-isoleucine and 20 to 40 parts L-valine or 10 to 30 parts L-isoleucine, 25 to 45 parts L-leucine, 5 to 15 parts L-phenylalanine and 5 to 15 parts L-tryptophan, and peptides with the sequences GKHQQEEENEGG (SEQ ID NO: 1), NFNNQLDQTPR (SEQ ID NO: 2), AGNPDIEHPE (SEQ ID NO: 3), NALEPDHRVE (SEQ ID NO: 4), GNPDIEHP (SEQ ID NO: 5), IYPGCPST (SEQ ID NO: 6), KLHENIAR (SEQ ID NO: 7), LAGNQEQE (SEQ ID NO: 8), ALEPDHR (SEQ ID NO: 9), EQGGEQG (SEQ ID NO: 10), EQPQQNE (SEQ ID NO: 11), IGTLAGA (SEQ ID NO: 12), NAMFVPH (SEQ ID NO: 13), GMIYPG (SEQ ID NO: 14), HNIGQT (SEQ ID NO: 15), IYPGCP (SEQ ID NO: 16), NALKPD (SEQ ID NO: 17), FIQGV (SEQ ID NO: 18), NALPE (SEQ ID NO: 19), NNEDT (SEQ ID NO: 20), SAEFG (SEQ ID NO: 21), SIIDT (SEQ ID NO: 22), YEGNS (SEQ ID NO: 23), LLLL (SEQ ID NO: 24), NLQG (SEQ ID NO: 25), SDNF (SEQ ID NO: 26), EGG, GAL, GGL, KPF, LLL, PPG, AD, EG, EY, GE, GF, GI, IA, IP, IS, KP, LK, PR, PY, RG, RP, RR, VF, VI, W, VY, VEELKPTPEGDLEIL (SEQ ID NO: 27), LKP, LVL, DL, ID, LD, LE, LV, WE, QLFGPNVNPWHNP (SEQ ID NO: 28), QLFNPSTNPWHSP (SEQ ID NO: 29), GGRGPPFIVGG (SEQ ID NO: 30), QLFNPSTNPWH (SEQ ID NO: 31), GGRGPPFIV (SEQ ID NO: 32), QLFNPSTNP (SEQ ID NO: 33), RGPPFIVGG (SEQ ID NO: 34), RGPPGGGFF (SEQ ID NO: 35), GGRPFFGG (SEQ ID NO: 36), QLFNPS (SEQ ID NO: 37), GFG, GLL, GW, LQL, RPG, EF, FG, FV, GL, GR, GV, IE, II, IL, IQ, LF, LI, RF, VA, WF, YF, YG, AQTQSLVYPFPGPIPNSLPQNIPPLTQ (SEQ ID NO: 38), YQQPVLGPVRGPFPIIV (SEQ ID NO: 39), PVLGPVRGPFPIIV (SEQ ID NO: 40), SLVYPFPGPIHNS (SEQ ID NO: 41), VPLGTQYTDAPSF (SEQ ID NO: 42), FFVAPFPEVFGK (SEQ ID NO: 43), FFVAPFPQVFGK (SEQ ID NO: 44), LVYPFPGPIHN (SEQ ID NO: 45), PVRGPFPIIV (SEQ ID NO: 46), VYPFPGPIPN (SEQ ID NO: 47), VYPFPPIGNH (SEQ ID NO: 48), YLGYLEQLLR (SEQ ID NO: 49), YPFPGPIHNS (SEQ ID NO: 50), YPFPGPIPNS (SEQ ID NO: 51), PFPGPIPNS (SEQ ID NO: 52), YPFPGPHIN (SEQ ID NO: 53), YPFPGPIPN (SEQ ID NO: 54), FALPQYLK (SEQ ID NO: 55), GPVRGPFP (SEQ ID NO: 56), LGYLEQLL (SEQ ID NO: 57), RGPFPIIV (SEQ ID NO: 58), RGPGPIIV (SEQ ID NO: 59), APFPEVF (SEQ ID NO: 60), AYFYPEL (SEQ ID NO: 61), FYPELFR (SEQ ID NO: 62), PFPGPIP (SEQ ID NO: 63), RGPFPIV (SEQ ID NO: 64), YPFPGPI (SEQ ID NO: 65), PVLGPV (SEQ ID NO: 66), VRGPFP (SEQ ID NO: 67), FYPELF (SEQ ID NO: 68), GPFPIV (SEQ ID NO: 69), PFPGPI (SEQ ID NO: 70), PFPIIV (SEQ ID NO: 71), DIKQM (SEQ ID NO: 72), EIVPN (SEQ ID NO: 73), NENLL (SEQ ID NO: 74), PGPIP (SEQ ID NO: 75), EVLN (SEQ ID NO: 76), LPQE (SEQ ID NO: 77), VYPF (SEQ ID NO: 78), APK, EEN, FLL, FPK, FPP, LRF, LRL, PFP, PGP, PPF, RGP, VW, VYP, YPF, AF, AL, AV, DA, EI, EL, FF, FI, FL, FP, FY, GP, GY, IF, IG, IK, IN, IT, IV, KF, LG, LW, LY, MI, PF, PI, PK, PL, PP, RL, SL, VD, VE, VL, YP, YY, GPFPVI (SEQ ID NO: 79), FALPEYLK (SEQ ID NO: 80), VG, RGPPFIV (SEQ ID NO: 81), GRP, FFF, WW, WWW, YPFP (SEQ ID NO: 82), FPF, IPAVF (SEQ ID NO: 83), LLF or YGLF (SEQ ID NO: 84).

According to the meaning of the 1-letter-code for amino acid sequences (as previously used for indicating the bitter peptides to be masked according to the invention), which is known to the person skilled in the art, the following meanings apply:

Alanine A
Arginine R
Asparagine N
Aspartic acid D
Cysteine C
Glutamine Q
Glutamic acid E
Glycine G
Histidine H
Isoleucine I
Leucine L
Lysine K
Methionine M
Phenylalanine F
Proline P
Serine S
Threonine T
Tryptophan W
Tyrosine Y
Valine V In the scope of the present text, masking is to be understood as a reduction, i.e. a decrease, or a complete suppression. Masking the unpleasant taste impression thus means to usually result in an improvement of the taste impression, in particular relating to bitter, astringent, doggy, dusty, dry, floury, rancid and/or metallic taste impressions.

For the above mentioned peptides, the N-terminal end of the peptide is directed on the left side, according to the common notation. Furthermore, the typical abbreviations for the amino acids are used.

Particularly preferred and particularly suited according to the invention are the compounds 2,4-Dihydroxy-N-[(4-hydroxy-3-methoxy-phenyl)methyl]benzamide (compound 1),
5,7-Dihydroxy-3-[(4-hydroxy-3-methoxy-phenyl)methyl]-1,3-benzoxazin-2,4-dione (compound 2),
4-Hydroxy-N-[(4-hydroxy-3-methoxy-phenyl)methyl]benzamide (compound 3) and
2-Hydroxy-N-[(4-hydroxy-3-methoxy-phenyl)methyl]benzamide (compound 4)
and their salts.

For clarification, the structures of the compounds 1 to 4 are subsequently listed:

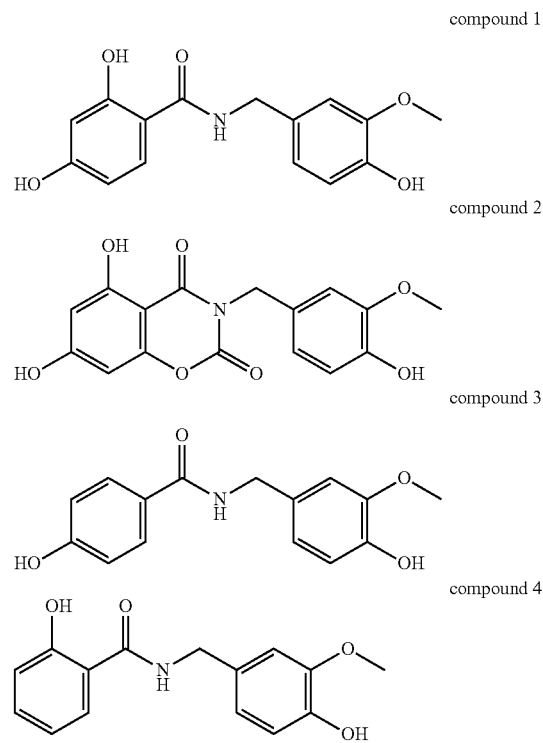

compound 1 compound 2 compound 3 compound 4

Unpleasant tasting peptides or, respectively, mixtures of amino acids as described herein are such that (a) taste bitter, astringent, doggy, dusty, dry, floury, rancid and/or metallic and/or (b) have a bitter, astringent, doggy, dusty, dry, floury, rancid and/or metallic aftertaste.

The unpleasant tasting peptides or, respectively, mixtures of amino acids can have further, usually not unpleasant taste and/or olfactory qualities. As further not unpleasant taste qualities for the purpose of the present invention, e.g. the impressions spicy, umami, sweet, salty, sour, hot (spicy), cooling, warming, burning or tingling are to be mentioned.

It was particularly surprising that the compounds of formula (I) and their salts to be used according to the invention are advantageously suitable for masking unpleasant taste impressions of the peptides or, respectively, mixtures of amino acid as described herein. In the example section below, comparative data for further bitter peptides—not included in the list according to claim 1—the taste of which is not reduced, and comparative data for a compound not being covered by formula (I), as described herein, are shown (proving that structurally similar compounds not to be used according to the invention are not—or not that well—suitable to mask the bitter taste of the peptides of the list according to claim 1, compared to compounds to be used according to the invention).

In salts of a hydroxybenzoic acid amide of the above formula (I) to be used according to the invention, one, more or all hydroxyl groups of the hydroxybenzoic acid amide are deprotonated. Thus, a corresponding amount of counter ions is present, wherein these are preferably selected from the group consisting of Na+ and K+.

Of course, the different hydroxybenzoic acid amides and their salts to be used according to the invention can each be used, according to the invention, alone or as mixtures.

It was surprisingly found that the hydroxybenzoic acid amides to be used according to the invention can reduce or even completely suppress the unpleasant taste impression, particularly the bitter taste impression already in very low concentrations, wherein it is of particular advantage that the hydroxybenzoic acid amides and their salts to be used according to the invention do almost not have an original taste in such concentrations and do not influence the further, usually not unpleasant taste qualities. Thus it is desired in the scope of the present invention and according to a preferred aspect, that the concentration of the hydroxybenzoic acid amides and their salts to be used according to the invention is in a range, in which the hydroxybenzoic acid amides and their salts do (almost) not have an original taste.

Preferably, the hydroxybenzoic acid amides and their salts described herein are used in combination with one, two or more further substances for masking an unpleasant, particularly bitter, taste impression of one or more unpleasant tasting substances, preferably such as described further below.

Particularly preferably, the hydroxybenzoic acid amides and their salts described herein are used (for preferred amounts of hydroxybenzoic acid amides and their salts see further below) in a composition selected from the group consisting of oral pharmaceutical or cosmetic preparations (finished product) serving for nutrition or oral care and for the application in the head area, and semi-finished products, particularly such serving for the production of oral pharmaceutical or cosmetic preparations (finished product) serving for nutrition or oral care and for the application in the head area, preferably in form of an olfactory, aromatic or flavour composition or seasoning mix.

A further aspect of the present invention relates to such compositions.

Such a composition is selected from the group consisting of (A) oral pharmaceutical or cosmetic preparations (finished product) serving for nutrition or oral care and for the application in the head area, and (B) semi-finished products, particularly such serving for the production of oral pharmaceutical or cosmetic preparations (finished product) serving for nutrition or oral care and for the application in the head area, preferably in form of a olfactory, aromatic or flavour composition or seasoning mix, comprising (i) one, two or more different hydroxybenzoic acid amides of formula (I), as defined above, or one, two or more different salts of one, two or more different hydroxybenzoic acid amides of formula (I), as defined above, or a mixture of one, two or more different hydroxybenzoic acid amides of formula (I), as defined above, with one, two or more different salts of one, two or more different hydroxybenzoic acid amides of formula (I), as defined above, in an amount of (A) 0.0001 to 0.5 wt.-%, preferably 0.001 to 0.1 wt.-%, related to the total weight of the composition (finished product), or, respectively, (B) 0.0001 to 95 wt.-%, preferably 0.001 to 80 wt.-%, particularly preferably 0.01 to 50 wt.-%, related to the total weight of the semi-finished product, and (ii) one or more unpleasant tasting substances of the group consisting of mixtures of amino acids comprising or consisting of each related to the weight, 40 to 50 parts L-leucine, 20 to 30 parts L-isoleucine and 20 to 40 parts L-valine or 10 to 30 parts L-isoleucine, 25 to 45 parts L-leucine, 5 to 15 parts L-phenylalanine and 5 to 15 parts L-tryptophan, and peptides with the sequences GKHQQEEENEGG, NFNNQLDQTPR, AGNPDIEHPE, NALEPDHRVE, GNPDIEHP, IYPGCPST, KLHENIAR, LAGNQEQE, ALEPDHR, EQGGEQG, EQPQQNE, IGTLAGA, NAMFVPH, GMIYPG, HNIGQT, IYPGCP, NALKPD, FIQGV, NALPE, NNEDT, SAEFG, SIIDT, YEGNS, LLLL, NLQG, SDNF, EGG, GAL, GGL, KPF, LLL, PPG, AD, EG, EY, GE, GF, GI, IA, IP, IS, KP, LK, PR, PY, RG, RP, RR, VF, VI, W, VY, VEELKPT-PEGDLEIL, LKP, LVL, DL, ID, LD, LE, LV, WE, QLFGPNVNPWHNP, QLFNPSTNPWHSP, GGRGPP-FIVGG, QLFNPSTNPWH, GGRGPPFIV, QLFNPSTNP, RGPPFIVGG, RGPPGGGFF, GGRPFFGG, QLFNPS, GFG, GLL, GW, LQL, RPG, EF, FG, FV, GL, GR, GV, IE, II, IL, IQ, LF, LI, RF, VA, WF, YF, YG, AQTQS-LVYPFPGPIPNSLPQNIPPLTQ, YQQPVLGPVRGPF-PIIV, PVLGPVRGPFPIIV, SLVYPFPGPIHNS, VPL-GTQYTDAPSF, FFVAPFPEVFGK, FFVAPFPQVFGK, LVYPFPGPIHN, PVRGPFPIIV, VYPFPGPIPN, VYP-FPPIGNH, YLGYLEQLLR, YPFPGPIHNS, YPFPG-PIPNS, PFPGPIPNS, YPFPGPHIN, YPFPGPIPN, FALPQYLK, GPVRGPFP, LGYLEQLL, RGPFPIIV, RGPGPIIV, APFPEVF, AYFYPEL, FYPELFR, PFPG-PIP, RGPFPIV, YPFPGPI, PVLGPV, VRGPFP, FYPELF, GPFPIV, PFPGPI, PFPIIV, DIKQM, EIVPN, NENLL, PGPIP, EVLN, LPQE, VYPF, APK, EEN, FLL, FPK, FPP, LRF, LRL, PFP, PGP, PPF, RGP, VW, VYP, YPF, AF, AL, AV, DA, EI, EL, FF, FI, FL, FP, FY, GP, GY, IF, IG, IK, IN, IT, IV, KF, LG, LW, LY, MI, PF, PI, PK, PL, PP, RL, SL, VD, VE, VL, YP, YY, GPFPVI, FALPEYLK, VG, RGPPFIV, GRP, FFF, WW, WWW, YPFP, FPF, IPAVF, LLF or YGLF,
in an amount of
(A) 0.001 to 10 wt.-%, preferably at least 0.005 wt.-%, at least 0.01 wt.-%, at least 0.05 wt.-%, at least 0.1 wt.-%, at least 0.5 wt.-% or at least 1 wt.-%, related to the total weight of the composition (finished product), or, respectively,
(B) 0.001 to 95 wt.-%, preferably 0.01 to 80 wt.-%, particularly preferably 0.1 to 50 wt-%, related to the total weight of the semi-finished product.

Particularly relevant are compositions according to the invention additionally comprising one, two or more further substances not according to formula (I) for masking an unpleasant, particularly bitter, taste impression of one or more unpleasant tasting substances.

According to the embodiments above, compositions according to the invention are preferred, wherein the or, respectively, one, two, more or all of the hydroxybenzoic acid amides of formula (I) or, respectively, their salt(s) is/are independent of each other selected from the group consisting of
2,4-Dihydroxy-N-[(4-hydroxy-3-methoxy-phenyl)methyl] benzamide (compound 1),
5,7-Dihydroxy-3-[(4-hydroxy-3-methoxy-phenyl)methyl]-1,3-benzoxazin-2,4-dione (compound 2),
4-Hydroxy-N-[(4-hydroxy-3-methoxy-phenyl)methyl]benzamide (compound 3) and
2-Hydroxy-N-[(4-hydroxy-3-methoxy-phenyl)methyl]benzamide (compound 4)
and their salts.

It is further preferred, if for the or, respectively, one, two, more or all salts of one, two or more different hydroxybenzoic acid amides of formula (I), as defined above, independently applies that the counter ion(s) of the or, respectively, one, more or all of the salts is/are selected from the group consisting of $Na^+$ and $K^+$.

It is particularly preferred for the purposes of the invention described herein, if the weight ratio of the total amount of component (i) to the total amount of component (ii) of the composition is in a range of 1:100,000 to 1:500, preferably in a range of 1:10,000 to 1:50.

According to one aspect of the present invention, it is preferred, if the amount of component (ii) is sufficient to be perceived as unpleasant, preferably bitter, taste in a comparative composition, not comprising component (i), but otherwise having an identical composition of the ingredients, and/or wherein the amount of component (i) is sufficient to mask the unpleasant, preferably bitter, taste impression of the unpleasant, preferably bitter, tasting substance(s) according to component (ii), compared to the comparative composition not comprising component (i).

The compositions for the purpose of the present invention can be present as capsules, tablets (non-coated as well as coated tablets, e.g. enteric-coated), lozenges, granulates, pellets, solid mixtures, dispersions in liquid phases, as emulsions, as powder, as solutions, as pastes or as other swallowable or chewable compositions, e.g. as food supplement. Especially applications rich in amino acids and peptides are preferred, particularly milk products (such as yoghurts, quarks), e.g. such with increased proportions of proteins or, respectively, amino acids (up to 10 wt.-% of the protein proportion in the product), furthermore sports nutrition (e.g. powder for preparing shakes, bars, gels and other types of preparations), e.g. such with an increased proportion of proteins or, respectively, amino acids (10-15 wt.-% of the protein or, respectively, amino acid proportion).

Suitable preparations serving for nutrition or pleasure and according to the present invention are e.g. bakery products (e.g. bread, dry biscuits, cake, other pastries), confectionery (e.g. chocolates, chocolate bar products, other bar products, fruit gum, hard and soft caramel, chewing gum), alcoholic or non-alcoholic drinks (e.g. coffee, tea, wine, drinks containing wine, beer, drinks containing beer, liqueurs, schnapps, brandies, lemonades containing fruit, isotonic drinks, refreshing drinks, nectars, fruit and vegetable juices, fruit and vegetable juice preparations), instant drinks (e.g. instant cocoa drinks, instant tea drinks, instant coffee drinks), meat products (e.g. ham, fresh sausage or raw sausage preparations, flavoured or marinated fresh or salt meat products), eggs or egg products (dry egg, protein, yolk), cereal products (e.g. breakfast cereals, muesli bars, precooked instant rice products), milk products (e.g. milk drinks, milk ice cream, yoghurt, kefir, cream cheese, soft cheese, hard cheese, dry milk powder, whey, butter, buttermilk, partly or completely hydrolysed products containing milk protein), products made of soy protein or other soy bean fractions (e.g. soy milk and products obtained therefrom, compositions containing soy lecithin, fermented products as tofu or tempe or products made therewith), fruit preparations (e.g. jams, fruit ice cream, fruit sauces, fruit fillings), vegetable preparations (e.g. ketchup, sauces, dry vegetables, frozen vegetables, precooked vegetables, boiled down vegetables), snacks (e.g. baked or fried potato chips or potato dough products, extrudates based on corn or peanut), products based on fat and oil or emulsions thereof (e.g. mayonnaise, remoulade, dressings), other finished products and soups (e.g. dry soups, instant soups, precooked soups).

Oral pharmaceutical preparations for the purpose of the present invention are preferably preparations present as capsules, tablets (non-coated as well as coated tablets, e.g. enteric-coated), lozenges, granulates, pellets, solid mixtures, dispersions in liquid phases, as emulsions, as powder, as solutions, as pastes or as other swallowable or chewable compositions and are used as food supplements, sports nutrition or medical food, available only on prescription, sold only in pharmacies or other medicinal products.

Preparations for the purpose of the present invention serving for oral care, are preferably mouth or dental care products such as toothpastes, tooth gels, tooth powder, mouthwashs, chewing gums and other oral care products.

Cosmetic preparations for the application in the head area are particularly such containing an unpleasant tasting substance and which can, even when properly applied to the skin, be contacted with the oral cavity, as for example cosmetic preparation for the application in the head area such as soaps, other cleaning or car products for the face area, face creams or lotions or ointments, sun protection products, beard cleaning or care products, shaving foams, shaving soaps or shaving gels, lipsticks or other lip cosmetics or lip care products.

The preparations for the purposes of the present invention can also be present as semi-finished products for preparing preparations serving for nutrition or pleasure, e.g. as spices, seasoning mixes as well as particularly seasonings, which are for instance used in the field of snacks. Additionally, olfactory, aromatic or flavour compositions are to be mentioned as preferred embodiments according to the present invention.

The preparations described herein can additionally contain further usual active substances, basic materials, excipients and additives for preparations serving for nutrition, pleasure or oral care or oral pharmaceutical or cosmetic preparations in the head area, particularly such as listed further below, preferably in amounts of 4 to 99.999 wt.-%, preferably 10 to 80 wt.-%, related to the total weight of the preparations. Furthermore, the preparations can contain water in an amount of up to 99.999 wt.-%, preferably 5 to 80 wt.-%, related to the total weight of the preparations.

The preparations according to the invention comprising one or more of the hydroxybenzoic acid amides and/or their salts to be used according to the invention are preferably produced by adding the hydroxybenzoic acid amides and/or their salts to be used according to the invention as substances, as solution or as a mixture with a solid or liquid carrier into a base preparation serving for nutrition, oral care or pleasure or an oral pharmaceutical or cosmetic base preparation. Advantageously, preparations according to the invention present as solution can also be transformed into a solid preparation by spray drying.

According to another preferred embodiment, the hydroxybenzoic acid amides and/or their salts to be used according to the invention and optionally further components of the preparation according to the invention are added into emulsions, liposomes, e.g. starting from phosphatidyl choline, microspheres, nanospheres or capsules, granulates or extrudates of a matrix suitable for foodstuff and luxury foods, e.g. made of starch, starch derivatives, cellulose or cellulose derivatives (e.g. hydroxypropyl cellulose), other polysaccharides (e.g. alginate), natural fats, natural waxes (e.g. beeswax, carnauba wax) or proteins, for producing preparations according to the invention.

In a further preferred production method, the hydroxybenzoic acid amides and/or their salts are first complexed with one or more suitable complexing agents, for example with cyclodextrins or cyclodextrin derivatives, preferably β-cyclodextrin, and are used in such a complexed form.

Particularly preferred is a preparation according to the invention, for which the matrix is selected in a way that the hydroxybenzoic acid amides and/or their salts are released from the matrix in a delayed way, so that a long-lasting effect is achieved.

Typical basic materials, excipients and additives can be used as further components of preparations according to the invention, particularly preparations serving for nutrition or pleasure, such as e.g. water, mixtures of fresh or processed, vegetable or animal basic or raw materials (e.g. raw, roasted, dried, fermented, smoked and/or cooked meat, bone, cartilage, fish, vegetable, fruit, herbs, nuts, vegetable or fruit juices or pastes or mixtures thereof), digestible or indigestible carbohydrates (e.g. sucrose, maltose, fructose, glucose, dextrins, amylose, amylopectin, inulin, xylanes, cellulose), sugar alcohols (e.g. sorbit), natural or hardened fats (e.g. sebum, lard, palm fat, coconut oil, hardened vegetable fat), oils (e.g. sunflower oil, peanut oil, corn oil, olive oil, fish oil, soy oil, sesame oil), fatty acids or their salts (e.g. potassium stearate), proteinogenic or non-proteinogenic amino acids and related compounds (e.g. taurine), further peptides, native or processed proteins (e.g. gelatine), enzymes (e.g. peptidases), nucleic acids, nucleotides, taste correctants for unpleasant taste impressions, taste correctants for usually non-unpleasant taste impressions, taste modulating substances (e.g. inositol phosphate, nucleotides such as guanosine monophosphate, adenosine monophosphate or other substances as sodium glutamate or 2-phenoxy propionic acid), emulsifiers (e.g. lecithins, diacylglycerols), stabilizers (e.g. carrageenan, alginate), preservatives (e.g. benzoic acid, sorbic acid), antioxidants (e.g. tocopherol, ascorbic acid), chelators (e.g. citric acid), organic or inorganic acidifiers (e.g. malic acid, acetic acid, citric acid, tartaric acid, phosphoric acid), additional bitter substances (e.g. quinin, caffeine, limonin, amarogentin, humolones, lupolones, catechines, tannins), sweeteners (e.g. saccharin, cyclamate, aspartame, neotame), mineral salts (e.g. sodium chloride, potassium chloride, magnesium chloride, sodium phosphate), substances preventing enzymatic tanning (e.g. sulphite, ascorbic acid), ethereal oils, plant extracts, natural or synthetic dyes or colour pigments (e.g. carotinoids, flavonoids, anthocyans, chlorophyll and their derivatives), spices, trigeminally effective substances or plant extracts, comprising such trigeminally effective substances, synthetic, natural or nature-identical flavours or fragrances as well as odour correctants.

Dental care agents (as base for preparations serving for oral care) containing the hydroxybenzoic acid amides and/or their salts to be used according to the invention, generally comprise an abrasive system (abrasives or polishing agents), such as silicic acid, calcium carbonates, calcium phosphates, aluminium oxides and/or hydroxylapatites, surface active substances, such as sodium lauryl sulfate, sodium lauryl sarcosinate and/or cocamidopropyl betaine, humectants such as glycerine and/or sorbit, thickeners, such as carboxymethyl cellulose, polyethylene glycol, carrageenan and/or LaponiteO, sweeteners, such as saccharin, taste correctants for unpleasant taste impressions, taste correctants for usually non-unpleasant taste impressions, taste modulating substances (e.g. inositol phosphate, nucleotides such as guanosine monophosphate, adenosine monophosphate or other substances as sodium glutamate or 2-phenoxy propionic acid), cooling agents such as menthol or menthol derivatives, stabilizers and active substances, such as sodium fluoride, sodium monofluorine phosphate, tin difluoride, quartemary ammonium fluorides, zinc citrate, zinc sulfate, tin pyrophosphate, tin dchloride, mixtures of different pyrophosphates, triclosan, cetylpyridinium chloride, aluminium lactate, potassium citrate, potassium nitrate, potassium chloride, strontium chloride, hydrogen peroxide, aromas and/or sodium bicarbonate or odour correctants.

Chewing gums (as a further example for preparations serving for oral care), which contain hydroxybenzoic acid amide and/or their salts to be used according to the invention, generally comprise a chewing gum base, i.e. a chewable base which becomes plastic while chewing, sugars of different kinds, sugar substitutes, sweeteners, sugar alcohols, taste correctants for unpleasant taste impressions, taste correctants for usually non-unpleasant taste impressions, taste modulating substances (e.g. inositol phosphate, nucleotides such as guanosine monophosphate, adenosine monophosphate or other substances as sodium glutamate or 2-phenoxy propionic acid), humectants, thickeners, emulsifiers, aromas and stabilizers or odour correctants.

As components for oral pharmaceutical preparations according to the invention, all typical further active substances, basic materials, excipients and additives for oral pharmaceutical preparations can be used. Particularly unpleasant tasting pharmaceutical active substances able for being formulated orally can be used as active substances. The active substances, basic materials, excipients and additives can be transferred to the oral application forms in typical manner, which frequently happens by the use of inert, non-toxic, pharmaceutically suitable excipients. Among thee are (among others) carriers (e.g. microcrystalline cellulos), solvents (e.g. liquid polyethylene glycols), emulsifiers (e.g. sodium dodecylsulfate), dispersing agents (e.g. polyvinyl pyrrolidone), synthetic and natural biopolymers (e.g. albumin), stabilizers (e.g. antioxidants such as ascorbic acid), dyes (e.g. inorganic pigments such as iron oxides) and odour correctants as well as taste correctants not relating to the bitter taste.

Preferably, the preparations according to the invention can contain an aromatic substance composition, an olfactory substance composition or a flavour composition for rounding and refining the taste and/or smell of the preparation. Suitable compositions contain e.g. synthetic, natural or nature-identical aromatic substances, olfactory substances or flavours as well as suitable excipients and carriers. It is thus particularly advantageous that a bitter or metallic taste impression, originating from the aromatic substances, olfactory substances or flavours contained in the preparations according to the invention, can be masked and thus the total sensory profile is improved.

Preparations according to the invention, present as semi-finished products, can advantageously serve for masking an unpleasant taste impression of finished product preparations, which are produced by using the semi-finished product preparation.

In a particularly preferred embodiment of the present invention, the hydroxybenzoic acid amides and/or their salts according to the invention are used in combination with at least one further substance for changing, masking or reducing the unpleasant taste impression of an unpleasant tasting substance in the preparations according to the invention. In this way, a particularly effective masking can be achieved. Particularly the combination of the hydroxybenzoic acid amides or, respectively, their salts to be used according to the invention and other taste correctants for unpleasant, particularly bitter, taste impressions is preferred. The further taste correctants can, for example, be selected from the following list: Nucleotides (e.g. adenosine-5'-monophosphate, cytidne-5'-monophosphate), lactisole, sodium salts (e.g. sodium chloride, sodium lactate, sodium citrate, sodium acetate, sodium gluconoate), hydroxyflavanones (e.g. eryodictyol, homoeriodictyol or their sodium salts), amino acids or mixtures of whey proteins with lecithins.

In the scope of the present invention, also a method for (a) masking the unpleasant, particularly bitter, taste impression of one, two or more unpleasant, particularly bitter, tasting substances in a preparation according to the invention and/or (b) producing a preparation according to the invention is provided, with the following step:

Contacting or mixing the components (i) and (ii) as well as optionally further components (i) one, two or more different hydroxybenzoic acid amides of formula (I), as defined above, or one, two or more different salts of one, two or more different hydroxybenzoic acid amides of formula (I), as defined above, or a mixture of one, two or more different hydroxybenzoic acid amides of formula (I), as defined above, with one, two or more different salts of one, two or more different hydroxybenzoic acid amides of formula (I), as defined above, in an amount of (A) 0.0001 to 0.5 wt.-%, preferably 0.001 to 0.1 wt.-%, related to the total weight of the composition (finished product), or, respectively, (B) 0.0001 to 95 wt.-%, preferably 0.001 to 80 wt.-%, particularly preferably 0.01 to 50 wt.-%, related to the total weight of the semi-finished product, (ii) one or more unpleasant tasting substances of the group consisting of mixtures of amino acids comprising or consisting of each related to the weight, 40 to 50 parts L-leucine, 20 to 30 parts L-isoleucine and 20 to 40 parts L-valine or 10 to 30 parts L-isoleucine, 25 to 45 parts L-leucine, 5 to 15 parts L-phenylalanine and 5 to 15 parts L-tryptophan, and peptides with the sequences GKHQQEEENEGG, NFNNQLDQTPR, AGNPDIEHPE, NALEPDHRVE, GNPDIEHP, IYPGCPST, KLHENIAR, LAGNQEQE, ALEPDHR, EQGGEQG, EQPQQNE, IGTLAGA, NAMFVPH, GMIYPG, HNIGQT, IYPGCP, NALKPD, FIQGV, NALPE, NNEDT, SAEFG, SIIDT, YEGNS, LLLL, NLQG, SDNF, EGG, GAL, GGL, KPF, LLL, PPG, AD, EG, EY, GE, GF, GI, IA, IP, IS, KP, LK, PR, PY, RG, RP, RR, VF, VI, W, VY, VEELKPT-PEGDLEIL, LKP, LVL, DL, ID, LD, LE, LV, WE, QLFGPNVNPWHNP, QLFNPSTNPWHSP, GGRGPP-FIVGG, QLFNPSTNPWH, GGRGPPFIV, QLFNPSTNP, RGPPFIVGG, RGPPGGGFF, GGRPFFGG, QLFNPS, GFG, GLL, GW, LQL, RPG, EF, FG, FV, GL, GR, GV, IE, II, IL, IQ, LF, LI, RF, VA, WF, YF, YG, AQTQS-LVYPFPGPIPNSLPQNIPPLTQ, YQQPVLGPVRGPF-PIIV, PVLGPVRGPFPIIV, SLVYPFPGPIHNS, VPL-GTQYTDAPSF, FFVAPFPEVFGK, FFVAPFPQVFGK, LVYPFPGPIHN, PVRGPFPIIV, VYPFPGPIPN, VYP-FPPIGNH, YLGYLEQLLR, YPFPGPIHNS, YPFPG-PIPNS, PFPGPIPNS, YPFPGPHIN, YPFPGPIPN, FALPQYLK, GPVRGPFP, LGYLEQLL, RGPFPIIV, RGPGPIIV, APFPEVF, AYFYPEL, FYPELFR, PFPG-PIP, RGPFPIV, YPFPGPI, PVLGPV, VRGPFP, FYPELF, GPFPIV, PFPGPI, PFPIIV, DIKQM, EIVPN, NENLL, PGPIP, EVLN, LPQE, VYPF, APK, EEN, FLL, FPK, FPP, LRF, LRL, PFP, PGP, PPF, RGP, VW, VYP, YPF, AF, AL, AV, DA, EI, EL, FF, FI, FL, FP, FY, GP, GY, IF, IG, IK, IN, IT, IV, KF, LG, LW, LY, MI, PF, PI, PK, PL, PP, RL, SL, VD, VE, VL, YP, YY, GPFPVI, FALPEYLK, VG, RGPPFIV, GRP, FFF, WW, WWW, YPFP, FPF, IPAVF, LLF or YGLF, in an amount of (A) 0.001 to 10 wt.-%, preferably at least 0.005 wt.-%, at least 0.01 wt.-%, at least 0.05 wt.-%, at least 0.1 wt.-%, at least 0.5 wt.-% or at least 1 wt.-%, related to the total weight of the composition (finished product), or, respectively, (B) 0.001 to 95 wt.-%, preferably 0.01 to 80 wt.-%, particularly preferably 0.1 to 50 wt-%, related to the total weight of the semi-finished product.

The above mentioned in the context of preparations and uses according to the invention thereby also applies for preferred embodiments of the method.

Thus for example, a method according to the invention is preferred, wherein the, one, two, more or all of the hydroxybenzoic acid amide(s) of formula (I) or, respectively, their salt(s) is/are independently selected from the group consisting of 2,4-Dihydroxy-N-[(4-hydroxy-3-methoxy-phenyl)methyl] benzamide (compound 1), 5,7-Dihydroxy-3-[(4-hydroxy-3-methoxy-phenyl)methyl]-1,3-benzoxazin-2,4-dione (compound 2), 4-Hydroxy-N-[(4-hydroxy-3-methoxy-phenyl)methyl]benzamide (compound 3) and 2-Hydroxy-N-[(4-hydroxy-3-methoxy-phenyl)methyl]benzamide (compound 4)

and their salts.

Furthermore and preferably, it applies for the, one, two, more or all salts of one, two or more different hydroxybenzoic acid amides of formula (I), as defined above, that the counter ion(s) of the, one, more or all of the salt(s) is/are selected from the group consisting of $Na^+$ and $K^+$.

The amount of component (ii) is preferably sufficient to be perceived as unpleasant, preferably bitter, taste in a comparative composition, not comprising component (i), but otherwise having an identical composition of the ingredients, and/or wherein the amount of component (i) is sufficient to mask the unpleasant, preferably bitter, taste impression of the unpleasant, preferably bitter, tasting substance(s) according to component (ii), compared to the comparative composition not comprising component (i).

Within the following section, the present invention is further described by means of selected examples. The examples, however, only serve for further clarification without limiting the invention.

EXAMPLES

Example 1: Effect of 2,4-Dihydroxy-N-[(4-hydroxy-3-methoxy-phenyl)methyl]benzamide (Compound 1),5,7-Dihydroxy-3-[(4-hydroxy-3-methoxy-phenyl)methyl]-1,3-benzoxazin-2,4-dione (Compound 2), 4-Hydroxy-N-[(4-hydroxy-3-methoxy-phenyl)methyl]benzamide (Compound 3), 2-Hydroxy-N-[(4-hydroxy-3-methoxy-phenyl)methyl]benzamide (Compound 4) and N-[(4-hydroxy-3-methoxy-phenyl)methyl]-2,4-dimethoxy-benzamide (Compound 5, Comparative Example) on the Bitterness of a Mixture of Amino Acids The masking effect of hydroxybenzoic acid amides (compounds 1-4) to be preferably used according to the invention as well as a comparative substance (compound 5) on a mixture of bitter amino acids (2 g/l L-Isoleucine; 3.5 g/l L-Leucine; 1 g/l L-Phenylalanine; 0.7 g/l L-Tryptophan in water) was evaluated by an panel of experts (n=13) (Evaluation 0 [not bitter] up to 10 [extremely bitter]). The tasting was performed with a nose clip, to exclude olfactory influences, and in a randomized duo-test. The bitterness of the mixture of amino acids was evaluated by the panel by 4.98±0,31 on a scale from 0 to 10.

| Sample | Bitter taste amino acid mixture | Bitter taste amino acid mixture + sample | Reduction of bitterness in % compared to the mixture of amino acids |
|---|---|---|---|
| 100 ppm 2,4-Dihydroxy-N-[(4-hydroxy-3-methoxy-phenyl)methyl]benzamide (compound 1) | 5.27 | 3.90 | −25.9 |
| 100 ppm 5,7-Dihydroxy-3-[(4-hydroxy-3-methoxy-phenyl)methyl]-1,3-benzoxazin-2,4-dione (compound 2) | 4.59 | 3.20 | −30.3 |
| 100 ppm 4-Hydroxy-N-[(4-hydroxy-3-methoxy-phenyl)methyl]benzamide (compound 3) | 4.82 | 4.11 | −14.1 |
| 100 ppm 2-Hydroxy-N-[(4-hydroxy-3-methoxy-phenyl)methyl]benzamide (compound 4) | 5.13 | 4.74 | −7.7 |
| 100 ppm N-[(4-hydroxy-3-methoxy-phenyl)methyl]-2,4-dimethoxy-benzamide (compound 5, comparative example) | 5.59 | 6.86 | 22.8 |

Example 2: Effect of 2,4-Dihydroxy-N-[(4-hydroxy-3-methoxy-phenyl)methyl]benzamide (Compound 1) and N-[(4-hydroxy-3-methoxy-phenyl)methyl]-2,4-dimethoxy-benzamide (Compound 5, Comparative Example) on the Bitter Taste of Peptides The masking effect of 2,4-Dihydroxy-N-[(4-hydroxy-3-methoxy-phenyl)methyl]benzamide (compound 1) and N-[(4-hydroxy-3-methoxy-phenyl)methyl]-2,4-dimethoxy-benzamide (compound 5) on the bitter taste of peptides was examined in a panel of experts (n=15) in randomized duo-tests. Therefore, solutions of bitter peptides in water with or without the addition of the exemplary substances were tasted and the perceived bitter taste was evaluated on a scale from 0 (not bitter) to 10 (extremely bitter).

With compound 1, a clear reduction of the bitterness could be achieved for a plurality of peptides (with the exception of the dipeptide Leu-Trp (confirmation of the data of Ley et al. (Ley et al., J Agr Food Chem 54, 8574-8579 (2006)) as well as the tripeptide Glu-Leu-Leu, which are added as comparative examples here). Compound 5 ((additional) comparative example) was not able to achieve a reduction of the bitterness for any of the peptides. For some, compound 5 even increased the bitter taste.

| Peptide | Bitter taste Peptide solution | Bitter taste peptide solution + 100 ppm (compound 1) | Reduction of bitterness compound 1 (%) | Bitter taste peptide solution + 100 ppm (compound 5) | Reduction of bitterness compound 5 (%) (comparative example) |
|---|---|---|---|---|---|
| Arg-Pro 0.1% (w/v) | 1.85 | 1.47 | −20.9 | 2.05 | 10.81 |
| Trp-Trp-Trp 0.01% (w/v) | 6.47 | 5.35 | −17.4 | 6.40 | −1.08 |
| Tyr-Pro-Phe-Pro 0.1% (w/v) | 4.48 | 3.43 | −23.3 | 4.68 | 4.46 |
| Leu-Trp 0.2% (w/v) (comparative example) | 6.8 | 6.5 | −4 | 7.1 | 4.41 |

-continued

| Peptide | Bitter taste Peptide solution | Bitter taste peptide solution + 100 ppm (compound 1) | Reduction of bitterness compound 1 (%) | Bitter taste peptide solution + 100 ppm (compound 5) | Reduction of bitterness compound 5 (%) (comparative example) |
|---|---|---|---|---|---|
| Glu-Leu-Leu 0.2% (w/v) (comparative example) | 5.3 | 5.1 | −3.77 | 5.6 | 5.66 |

Example 3: Effect of 2,4-Dihydroxy-N-[(4-hydroxy-3-methoxy-phenyl)methyl]benzamide (Compound 1) on the Bitter Taste of a Solution of Whey Protein Hydrolysate The bitter masking effect of 2,4-dihydroxy-N-[(4-hydroxy-3-methoxy-phenyl)methyl]benzamide (compound 1) on the bitter taste of whey protein hydrolysate was tested in a panel of experts [n=8] for a solution of 3% (w/v) of a commercially available whey protein hydrolysate (BioZate 3 of the company Davisco) in randomized duo-tests. The perceived bitter taste was evaluated on a scale from 0 [not bitter] to 10 [extremely bitter]. For comparison, a combination of compound 1 with a usual bitter masking aroma was tested, to examine possible additive effects.

| Sample | Reduction of the bitter taste [%] |
|---|---|
| Base [whey protein hydrolysate (3% (w/v) in water)] | 0 |
| Base + 100 ppm compound 1 | −24.5 |
| Base + bitter masking aroma (Symrise) (1.6% (w/v)) + 100 ppm compound 1 | −65.5 |

Application Example 1: Spray Dried Preparation as Semi-Finished Product for Aromatizing Finished Products According to the Invention

| Ingredient | Use in wt.-% |
|---|---|
| Drinking water | 60.8% |
| Maltodextrin of wheat | 24.3% |
| Gum Arabic | 6.1% |
| 2,4-Dihydroxy-N-[(4-hydroxy-3-methoxy-phenyl)methyl]benzamide (compound 1) | 8.8% |

The drinking water is provided in a container and the maltodextrin and Gum Arabic are dissolved therein. Subsequently, the 2,4-dihydroxy-N-[(4-hydroxy-3-methoxy-phenyl)methyl]benzamide (compound 1) is emulsified into the carrier solution with a turrax. The temperature of the spray solution should not exceed 30° C. The mixture is then spray dried (required temperature entering: 185-195° C., required temperature exit: 70-75° C.).

The spray dried semi-finished product contains approx. 19-22% of compound 1 and can be used for the production of a preparation according to the invention as described herein.

Application Example 2: Use in a Soy Drink

The compound 2,4-Dihydroxybenzoicacid-N-(4-hydroxy-3-methoxybenzyl)amide (compound 1) was pre-dissolved in ethanol and added to a soy milk from a local supermarket, which contains unpleasant tasting substances according to claim 1. The mixture was stirred in the beaker with the milk aroma.

| Ingredient | Use in wt.-% |
|---|---|
| Soy milk (local supermarket, contains in average approx . . . 15% free amino acids) | 99.8% |
| Milk aroma (Symrise) | 0.1% |
| 10% 2,4-Dihydroxybenzoicacid-N-(4-hydroxy-3-methontbenzyl)amide (compound 1) in ethanol | 0.1% |

Application Example 3: Use in a Soy Drink in Combination with γ-Amino Butyric Acid γ-amino butyric acid was pre-dissolved in water and 2,4-Dihydroxybenzoicacid-N-(4-hydroxy-3-methoxybenzyl)amide in ethanol and added to a soy milk from a local supermarket, which contains unpleasant tasting substances according to claim 1, according to the table (mixtures A-C). The mixtures were stirred in the beaker together with the milk aroma.

| | Use in wt.-% | | |
|---|---|---|---|
| Ingredient | A | B | C |
| Soy milk (local supermarket) | add to 100% | add to 100% | add to 100% |
| Milk aroma (Symrise) | 0.1% | 0.1% | 0.1% |
| 10% 2,4-Dihydroxybenzoicacid-N-(4-hydroxy-3-methoxybenzyl)amide in ethanol | 0.1% | — | 0.1% |
| 1% γ-amino butyric acid in water | 0.1% | — | — |

Compared to mixture B, the mixtures A and C were clearly less bitter. Additionally, in mixture A, the astringency and the beany taste were clearly reduced.

Application Example 4: Whey Protein Drink

Production of a fruit whey protein drink according to the following recipe with subsequent homogenization and pasteurization.

| | Use in wt.-% | |
|---|---|---|
| Ingredient | A | B |
| Whey protein isolate (min. 88% protein TS, contains unpleasant tasting substances according to claim 1) | 8% | 8% |

-continued

| Ingredient | Use in wt.-% A | B |
|---|---|---|
| Fruit juice concentrate mixture (mango, banana, carrot, orange) | 10% | 10% |
| Citric acid 50% | 0.2% | 0.2% |
| Pectin | 0.4% | 0.4% |
| Vitamin-mixture | 0.01% | 0.01% |
| Mineral salt-mixture | 1% | 1% |
| 10% 2,4-Dihydroxybenzoicacid-N-(4-hydroxy-3-methoxybenzyl)amide in ethanol | — | 0.1% |
| Mango aroma (Symrise) | 0.05% | 0.05% |
| Drinking water | Add to 100% | Add to 100% |

Compared to the comparative mixture A, mixture B was clearly less bitter.

Application Example 5: Highly Protein Containing Drink (Sports Nutrition)

The dry ingredients are mixed and subsequently dissolved in drinking water. In example C, the 10% solution of the 2,4-Dihydroxybenzoesäure-N-(4-hydroxy-3-methoxybenzyl)amide is added and stirred.

| Ingredient | Use in wt.-% A | B | C |
|---|---|---|---|
| Whey protein isolate (min. 88% protein TS, contains unpleasant tasting substances according to claim 1) | 8% | 8% | 8% |
| Mixture of amino acids (45% L-Leucine; 30% L-Valine, 25% L-Isoleucine) | 1% | 1% | 1% |
| Citric acid | 0.1% | 0.1% | 0.1% |
| Sucralose | 0.007% | 0.007% | 0.007% |
| Orange dry aroma (Symrise) | 0.1% | 0.1% | 0.1% |
| Bitter masking dry aroma (Symrise) | — | 1.6% | 1.6% |
| 10% 2,4-Dihydroxybenzoicacid-N-(4-hydroxy-3-methoxybenzyl)amide in ethanol | — | — | 0.1% |
| Drinking water | Add to 100% | Add to 100% | Add to 100% |

Compared to the comparative mixture A, the mixtures B and C are less bitter. Further, mixture C is clearly less bitter than mixture B.

Application Example 6: Dietary Foodstuff for Special Medical Purposes (FSMP)

Production of a UHT-drink according to the recipe below.

| Ingredient | Use in wt.-% A | B |
|---|---|---|
| Whey protein concentrate (min. 80% protein TS, contains unpleasant tasting substances according to claim 1) | 12% | 12% |
| Drinking water | Add to 100% | Add to 100% |
| Glucose syrup | 10% | 10% |
| Vegetable oils | 4% | 4% |
| Sucrose | 2% | 2% |
| Maltodextrin | 1.5% | 1.5% |
| Vitamin-mixture | 0.05% | 0.05% |
| Mineral salt-mixture | 2% | 2% |
| Vanilla aroma (Symrise) | 0.2% | 0.2% |
| Lecithin | 0.1% | 0.1% |
| Citric acid | 0.05% | 0.05% |
| 10% 2,4-Dihydroxybenzoicacid-N-(4-hydroxy-3-methoxybenzyl)amide in ethanol | — | 0.1% |

Mixture B is clearly less bitter and drying in the aftertaste compared to comparative mixture A.

Application Example 7: Protein Bar

The cereals and the whey protein isolate are mixed. A syrup is cooked from the remaining ingredients (without aroma and 2,4-Dihydroxybenzoicacid-N-(4-hydroxy-3-methoxybenzyl)amide). At the end of the cooking time, the aroma or, respectively, the 10% solution 2,4-Dihydroxybenzoicacid-N-(4-hydroxy-3-methoxybenzyl)amide in ethanol is added. The syrup is mixed with the cereals and formed into bars.

| Ingredient | Use in wt.-% A | B | C |
|---|---|---|---|
| Oat flakes | 13% | 13% | 13% |
| Rice-Crispies | 14% | 14% | 14% |
| Corn Flakes | 10% | 10% | 10% |
| Whey protein isolate (min. 88% protein TS, contains unpleasant tasting substances according to claim 1) | 10% | 10% | 10% |
| Glucose Syrup | 0.1% | 0.1% | 0.1% |
| Sucrose | 12% | 12% | 12% |
| Glycerine | 1% | 1% | 1% |
| Salt | 0.2% | 0.2% | 0.2% |
| Drinking water | 13.5% | 13.5% | 13.5% |
| Vegetable fat | 10% | 10% | 10% |
| Lecithin | 0.2% | 0.2% | 0.2% |
| Bitter masking aroma (Symrise) | — | — | 0.3% |

-continued

| Ingredient | Use in wt.-% | | |
|---|---|---|---|
| | A | B | C |
| Caramel aroma (Symrise) | 0.1% | 0.1% | 0.1% |
| 10% 2,4-Dihydroxybenzoicacid-N-(4-hydroxy-3-methoxybenzyl)amide in ethanol | | 0.1% | 0.1% |

Compared to the comparative mixture A, mixtures B and C are less bitter. Additionally, mixture C is clearly less drying and astringent in the aftertaste compared to mixture B.

Application Example 8: Highly Protein Containing Milk Product (Quark)

2,4-Dihydroxybenzoicacid-N-(4-hydroxy-3-methoxybenzyl)amide is pre-solved in ethanol and added while stirring into quark with the cream aroma. In the comparative mixture, only the cream aroma is added while stirring.

| Ingredient | Use in wt.-% | | |
|---|---|---|---|
| | A | B | C |
| Highly protein containing market product (contains unpleasant tasting substances according to claim 1); (French market) (9% protein, 2.9% fat) | Add to 100% | Add to 100% | Add to 100% |
| Sucrose | 4% | 4% | 4% |
| Cream aroma (Symrise) | 0.15% | 0.15% | 0.15% |
| 10% 2,4-Dihydroxybenzoicacid-N-(4-hydroxy-3-methoxybenzyl)amide in ethanol | — | 0.05% | 0.1% |

Compared to mixture A, mixtures B and C were clearly less bitter and astringent. In mixture C, the astringency was even more clearly reduced.

The invention claimed is:

1. A composition comprising:
   (i) 0.0001 to 0.5 wt. %, relative to the total weight of the composition, of 2,4-Dihydroxy-N-[(4-hydroxy-3-methoxy-phenyl)methyl]benzamide (compound 1), a salt thereof, or a mixture thereof; and
   (ii) 0.001 to 10 wt. %, relative to the total weight of YPFP (SEQ ID NO: 82), WWW, or a combination thereof;
   provided that the amount of component (i) is sufficient to mask an unpleasant taste impression of component (ii), compared to an otherwise identical comparative composition not comprising component (i).

2. The composition of claim 1, further comprising:
   (iii) one or more additional substances not of formula (I) that mask an unpleasant taste impression.

* * * * *